United States Patent
Kidmose et al.

(10) Patent No.: US 11,857,328 B2
(45) Date of Patent: Jan. 2, 2024

(54) ACTIVE ELECTRODE HAVING A CLOSED-LOOP UNIT-GAIN AMPLIFIER WITH CHOPPER MODULATION

(71) Applicant: T&W Engineering A/S, Lynge (DK)

(72) Inventors: Preben Kidmose, Aarhus (DK); Xiong Zhou, Aarhus (DK); Soren Kilsgaard, Lynge (DK); Qiang Li, Aarhus (DK)

(73) Assignee: T&W Engineering A/S, Lynge (DK)

( * ) Notice: Subject to any disclaimer, the term of this patent is extended or adjusted under 35 U.S.C. 154(b) by 0 days.

(21) Appl. No.: 15/626,621

(22) Filed: Jun. 19, 2017

(65) Prior Publication Data
US 2017/0281037 A1    Oct. 5, 2017

Related U.S. Application Data

(63) Continuation-in-part of application No. PCT/EP2014/078651, filed on Dec. 19, 2014.

(51) Int. Cl.
*A61B 5/00* (2006.01)
*A61B 5/291* (2021.01)
(Continued)

(52) U.S. Cl.
CPC ............... *A61B 5/291* (2021.01); *A61B 5/25* (2021.01); *A61B 5/30* (2021.01); *A61B 5/6803* (2013.01);
(Continued)

(58) Field of Classification Search
CPC . H03F 1/26; H03F 1/523; H03F 3/393; H03F 3/45179; H03F 3/45183;
(Continued)

(56) References Cited

U.S. PATENT DOCUMENTS

| 3,656,065 A * | 4/1972 | Reinhard | H03F 3/393 330/253 |
| 7,385,443 B1 * | 6/2008 | Denison | H03F 3/38 330/10 |

(Continued)

FOREIGN PATENT DOCUMENTS

| EP | 2 101 408 A1 | 9/2009 |
| JP | 2008/094271 A1 | 8/2008 |

(Continued)

OTHER PUBLICATIONS

Communication dated Sep. 26, 2018, issued by the Australian Patent Office in corresponding application No. 2014414404.

(Continued)

*Primary Examiner* — May A Abouelela
(74) *Attorney, Agent, or Firm* — Sughrue Mion, PLLC (57) ABSTRACT

An active electrode has an electrode for sensing an electric potential and generating an input signal, and a shield placed near the electrode but being electric insulated from the electrode. An integrated amplifier (10) has an input connected to the at least one electrode for receiving the input signal, and providing a buffered path outputting a buffered output signal. The shield being connected to the output of the integrated amplifier to actively drive the electrical potential of the shield, thereby providing an active shielding of the electrode. The buffered path includes a first mixer (11) in front of the integrated amplifier for frequency shifting the input signal from a basic frequency range to a higher frequency range, and a second mixer (12) on the output of the integrated amplifier for frequency shifting the amplified signal from the higher frequency range back to the basic frequency range. The active electrode may be used for recording EEG signals.

23 Claims, 6 Drawing Sheets

(51) Int. Cl.

| | |
|---|---|
| H03F 3/393 | (2006.01) |
| H03F 3/45 | (2006.01) |
| A61B 5/25 | (2021.01) |
| A61B 5/30 | (2021.01) |
| H03F 1/26 | (2006.01) |
| H03F 1/52 | (2006.01) |
| H03G 3/20 | (2006.01) |
| H04R 25/00 | (2006.01) |

(52) U.S. Cl.
CPC .............. *H03F 1/26* (2013.01); *H03F 1/523* (2013.01); *H03F 3/393* (2013.01); *H03F 3/45179* (2013.01); *H03F 3/45183* (2013.01); *H03F 3/45475* (2013.01); *H03G 3/20* (2013.01); *H04R 25/353* (2013.01); *H04R 25/505* (2013.01); *A61B 5/6817* (2013.01); *A61B 2562/0209* (2013.01); *H03F 2200/261* (2013.01); *H03F 2200/271* (2013.01); *H03F 2203/45306* (2013.01); *H04R 2225/43* (2013.01); *H04R 2225/67* (2013.01)

(58) Field of Classification Search
CPC ........... H03F 3/45475; H03F 2200/261; H03F 2200/271; H03F 2203/45036; H03F 3/38; H03F 2203/45306; H03G 3/20; H04R 25/353; H04R 25/505; H04R 2225/43; H04R 2225/67; A61B 2562/0209; A61B 5/0478; A61B 5/04004; A61B 5/0408; A61B 5/6803; A61B 5/6817; A61B 5/7203; A61B 5/31; A61B 5/308; A61B 5/28; A61B 5/7225; A61B 5/291; A61B 5/30; A61B 5/25
See application file for complete search history.

(56) References Cited

U.S. PATENT DOCUMENTS

| | | | |
|---|---|---|---|
| 7,456,684 B2 | 11/2008 | Fang et al. | |
| 7,761,145 B2* | 7/2010 | Virag | G16H 40/67 600/544 |
| 8,326,397 B2* | 12/2012 | Nakagawa | A61B 5/0476 600/383 |
| 8,608,984 B1* | 12/2013 | Taranekar | A61B 5/6891 252/514 |
| 10,143,396 B2* | 12/2018 | Chappell | A61B 5/6804 |
| 2003/0189461 A1 | 10/2003 | Huijsing et al. | |
| 2006/0176109 A1 | 8/2006 | Huijsing et al. | |
| 2006/0264775 A1* | 11/2006 | Mills | A61B 5/0537 600/509 |
| 2006/0276702 A1* | 12/2006 | McGinnis | A61B 5/296 600/372 |
| 2008/0001585 A1* | 1/2008 | Bakkaloglu | H03F 1/086 323/280 |
| 2008/0013747 A1* | 1/2008 | Tran | A61B 5/0295 381/67 |
| 2008/0027350 A1* | 1/2008 | Webler | A61B 5/283 600/547 |
| 2008/0077015 A1* | 3/2008 | Boric-Lubecke | G01S 13/888 600/453 |
| 2008/0159365 A1* | 7/2008 | Dubocanin | H03F 3/45475 330/109 |
| 2008/0180278 A1* | 7/2008 | Denison | A61B 5/7203 340/870.18 |
| 2009/0082691 A1* | 3/2009 | Denison | A61B 5/374 600/544 |
| 2009/0099627 A1 | 4/2009 | Molnar et al. | |
| 2010/0113898 A1* | 5/2010 | Kim | A61B 5/318 600/310 |
| 2010/0210947 A1* | 8/2010 | Burcher | A61N 1/3925 600/454 |
| 2010/0327887 A1 | 12/2010 | Denison et al. | |
| 2010/0331660 A1* | 12/2010 | Wada | A61B 5/6817 600/382 |
| 2011/0092834 A1* | 4/2011 | Yazicioglu | A61B 5/0531 600/509 |
| 2011/0204971 A1* | 8/2011 | Chang | H03G 1/0035 330/69 |
| 2012/0083690 A1* | 4/2012 | Semenov | B82Y 5/00 600/428 |
| 2012/0116198 A1* | 5/2012 | Veen | A61B 5/04284 600/372 |
| 2012/0157807 A1* | 6/2012 | Virtanen | A61B 5/276 600/372 |
| 2013/0296731 A1* | 11/2013 | Kidmose | A61B 5/6833 600/544 |
| 2013/0300435 A1* | 11/2013 | Chi | G01R 29/12 324/658 |
| 2014/0051961 A1* | 2/2014 | Badower | A61B 5/369 600/383 |
| 2014/0135593 A1* | 5/2014 | Jayalth | A61B 5/318 600/301 |
| 2014/0171775 A1* | 6/2014 | Kilsgaard | A61B 5/0478 600/379 |
| 2014/0276186 A1* | 9/2014 | Stanslaski | A61B 5/7225 600/544 |
| 2015/0141856 A1* | 5/2015 | Choi | A61B 5/318 600/509 |
| 2016/0007928 A1* | 1/2016 | Chiu | A61B 5/7246 600/386 |
| 2016/0081577 A1* | 3/2016 | Sridhar | A61B 5/6803 600/383 |
| 2016/0262703 A1* | 9/2016 | Maccallum | A61B 5/04004 |

FOREIGN PATENT DOCUMENTS

| | | |
|---|---|---|
| JP | 2010-517472 A | 5/2010 |
| JP | 2011-516109 A | 5/2011 |
| JP | 2012-532731 A | 12/2012 |
| JP | 2014-527862 A | 10/2014 |
| WO | 2009/112494 A1 | 9/2009 |
| WO | 2011/007292 A1 | 1/2011 |
| WO | 2013/026481 A1 | 2/2013 |

OTHER PUBLICATIONS

Christina Nickolas, "The Basics of Mixers", DigiKey, Sep. 13, 2014, 3 pages total [Online] https://web.archive.org/web/20140913105741/https://www.digikey.com.au/en/articles/techzone/2011/oct/the-basics-of-mixers.

Don Tuite, "Chopper-Stabilized Op Amps", Electronic Design, Jan. 21, 2013, 3 pages total [Online] https://web.archive.org/web/20130121091111/http://www.electronicdesign.com/analog/chopperstabilized-op-amps.

Communication dated May 29, 2018 from the Japanese Patent Office in counterpart Application No. 2017-549582.

Christian C Enz et al., "Circuit techniques for reducing the effects of op-amp imperfections: autozeroing, correlated double sampling, and chopper stabilization", Proceedings of the IEEE, Nov. 1996, pp. 1584-1614, vol. 84, No. 11.

Yu M. Chi et al., "Micropower Non-contact EEG Electrode with Active Common-Mode Noise Suppression and Input Capacitance Cancellation", 31st Annual International Conference of the IEEE EMBS, Sep. 2-6, 2009, pp. 4218-4221, Minneapolis, Minnesota, USA.

Yu M. Chi et al., "Ultra-High Input Impedance, Low Noise Integrated Amplifier for Noncontact Biopotential Sensing", IEEE Journal On Emerging and Selected Topics in Circuits and Systems, Dec. 2011, pp. 526-535, vol. 1, No. 4.

Shuo-Ting Kao et al., "A 1.5V 7.5uW Programmable Gain Amplifier for Multiple Biomedical Signal Acquisition", Biomedical Circuits and Systems Conference, 2009, BioCAS 2009. IEEE , Nov. 26-28, 2009, pp. 73-76.

Mcky Wong et al., "Lowest Noise Zero-Drift Amplifier Has 5.6 nV/√Hz Voltage Noise Density", Application note, AN-1114 @ 2011 Analog Devices, Inc.

(56) References Cited

OTHER PUBLICATIONS

Abdelkader Hadj Said et al., "Design of a Chopper Amplifier for Use in Biomedical Signal Acquisition", Electronics Diploma Electronics, A Thesis Submitted in Partial Fulfillment of the Requirements for the Master of Science Degree Department of Electrical and Computer Engineering in the Graduate School, Southern Illinois University Edwardsville, Edwardsville, Illinois, Dec. 2010.
International Search Report of PCT/EP2014/078651 dated Sep. 16, 2015 [PCT/ISA/210].
Written Opinion of PCT/EP2014/078651 dated Sep. 16, 2015 [PCT/ISA/237].
Communication dated Feb. 5, 2019, from the Japanese Patent Office in counterpart application No. 2017-549582.

* cited by examiner

ACTIVE ELECTRODE HAVING A CLOSED-LOOP UNIT-GAIN AMPLIFIER WITH CHOPPER MODULATION

CROSS REFERENCE TO RELATED APPLICATIONS

This application is a continuation in part of International Application No. PCT/EP2014/078651, filed on Dec. 19, 2014, the contents of which are incorporated herein by reference in their entirety.

BACKGROUND OF THE INVENTION

The present invention relates to an electric field sensor. The invention, more particularly, relates to electric field sensors for sensing an electric potential difference—e.g. a bio-potential signal—and generating an input signal for signal processing. The sense electrodes are guarded by an actively driven shield to minimize capacitive coupled noise and minimize the capacitive load of the source signal. Also, the invention relates to a sensor system for sensing an electric potential difference. Furthermore, the invention relates to a method for sensing an electric potential difference in a sensor system.

Active electrodes are widely used for bio-potential recordings, especially for advanced electrode technology like non-contact and dry-contact electrode. The purposes of employing active electrode are shielding the electrode from external interferences, and compensating the parasitic capacitances.

Compared with passive electrodes, active electrodes generally provide better immunity against surrounding interferences, in particular capacitive coupled interferences as for example Power Line Interference (PLI). Therefore, they are suitable for emerging applications in wearable bio-potential recording. And nowadays, active electrode combined with right-leg-driven technique is accepted as the main trend in the high-quality bio-signal recording. In general, an active electrode should hold several features including sufficient low input-referred noise, high input impedance and low bias current, low input referred offset, low output impedance, high Common Mode Rejection Ratio (CMRR) and Power Supply Rejection Ratio (PSRR), and for wearable devices a low power consumption.

CMRR of a differential amplifier is the rejection of unwanted input signals common to both input terminals, relative to the wanted difference signal. PSRR is the ratio between the change in supply voltage in the op-amp and the equivalent (differential) output voltage it produces. The output voltage will depend on the feedback circuit, and an ideal instrumentation amplifier would have infinite PSRR.

Electrocardiography (ECG) is a transthoracic recording of the electrical activity of the heart as a function of time. ECG signals are picked up by electrodes attached to the surface of the skin and recorded by a device external to the body. Electroencephalography (EEG) is the recording of electrical activity along the scalp, and EEG signals is a measure of the voltage fluctuations resulting from ionic current flows due to neuronal activity within the brain. Ear-EEG is attractive as the electrodes can be arranged in the ear-canal or around the ear in a device similar to a hearing aid.

Electrophysiological signals are normally weak in amplitude compared with surrounding interferences. Among regular physiology signals, ECG is relatively stronger typical with peak amplitudes in the 100 µV-1 mV range. EEG is weaker, in the range of 10 µV-100 µV. For Ear-EEG peak amplitudes are typically in the range of 1 µV-10 µV, which is approximately 20 dB below on-scalp EEG. However, the coupling interferences from surrounding could easily be in millivolt-level or even volt-level. Most of these interferences normally appear in common mode along with bio-signals. In principle, it's possible to pick up signals of interest clearly if electrodes and bio-amplifier are completely differential, but in any practical amplifier, the CMRR is not infinite. Therefore, the noise immunity is of significant importance for bio-signal recording.

In practice it is not possible to design an ideal instrumentation amplifier, and thus any amplifier will be designed to provide a good trade-off between the ideal parameters.

The purpose of the invention is to provide an electric field sensor with improved key performance metrics relative to the ideal instrumental amplifier. By providing such an electric field sensor, EEG and ear-EEG sensors can be developed and designed for daily use e.g. for detecting Hypoglycemia. This may assist e.g. diabetes patients to maintain a normal daily life.

SUMMARY OF THE INVENTION

An active electrode according to the invention comprises an electrode for sensing an electric potential and generating an input signal, a shield placed near said electrode and being electric insulated from said electrode, and an integrated amplifier having an input connected to said at least one electrode for receiving the input signal, and providing a buffered path outputting a buffered output signal. The shield being connected to said output of the integrated amplifier to actively drive the electrical potential of said shield, thereby providing an active shielding of said electrode. The buffered path includes a first mixer in front of the integrated amplifier for frequency shifting the input signal from a basic frequency range to a higher frequency range, and a second mixer on the output of the integrated amplifier for frequency shifting the amplified signal from said higher frequency range back to said basic frequency range.

The new technique proposed according to the invention provides a combination of the advantages from active electrodes designs with buffer and with chopper modulation amplifier, reaching a trade-off in key performances metrics.

Due to the finite input impedance of the amplifier, imbalance in electronic impedances leads to that part of the common mode signal will appear in differential mode on the input of the instrumentation amplifier. This is in particular the case in electrodes with high impedance as is the case for e.g. dry-contact and capacitive electrodes. Active shielding increases the input impedance, thereby increases the CMRR on the input of the amplifier, and thereby significantly diminishes this interference.

The active electrode design according to the invention provides several attractive advantages. Due to the unit-gain configuration of the amplifier configured as a choppered buffer, good shielding properties can be achieved. As a consequence, ultra-high input impedance is obtainable. The new active electrode design according to the invention provides improved Common Mode Rejection Ratio (CCMR) and improved Power Supply Rejection Ratio (PSRR) between two buffer channels, which is very important for the noise immunity against surrounding interferences.

Chopper modulation shielded by the buffered output leverages the voltage-domain and the current-domain accuracies, reaching a good trade-off compared to conventional techniques using buffer and chopper amplifier. Besides, a significant benefit resulting from chopper modulation is the improved CMRR and PSRR between two buffer channels, which could be quite useful to enhance the noise immunity against surrounding interferences.

A chopper spike filter (CSF) in front of a subsequent differential amplifier could filter out the accompanying chopper spikes and ripples at the expense of extra amount of power. An active electrode with choppered buffer according to the invention will be highly useful within high-quality bio-recording systems.

A buffer amplifier provides electrical impedance transformation from one circuit to another. If the voltage is transferred unchanged (the voltage gain $A_v$ is 1), the amplifier is a unity gain buffer. A unity gain amplifier (a buffer) is often implemented as a voltage follower as the output voltage follows or tracks the input voltage. Although the voltage gain of such a buffer amplifier may be (approximately) unity, it usually provides considerable current gain and thus power gain. A closed-loop unit-gain amplifier with chopper modulation according to the invention provides electrical impedance transformation, and acts as a voltage follower with a considerable current gain and thus power gain.

According to a further aspect of the invention there is provided a sensor system for sensing an electric potential difference. The sensor system comprises at least one set of electrodes including a reference electrode providing an electric potential reference and a sensing electrode providing a measurement point for measuring an electrical potential relative to the reference electrode. The sensor system further comprises a differential amplifier receiving input from the sensing electrode and the reference electrode and generating an output signal representing the electrical potential difference between the sensing electrode and the reference electrode. At least one electrode of the at least one set of electrodes being an active electrode, comprising an electrode for sensing an electric potential and generating an input signal, a shield placed near the electrode, and the shield being electric insulated from the electrode and an integrated amplifier having an input connected to the at least one electrode for receiving the input signal, and providing a buffered path outputting a buffered output signal. The shield is connected to the output of the integrated amplifier to actively drive the electrical potential of the shield, thereby providing an active shielding of the electrode. The buffered path includes a first mixer in front of the integrated amplifier for frequency shifting the input signal from a basic frequency range to a higher frequency range, and a second mixer on the output of the integrated amplifier for frequency shifting the amplified signal from the higher frequency range back to the basic frequency range.

According to a further aspect of the invention, there is provided a method of for sensing an electric potential difference in a sensor system having at least one set of electrodes including an reference electrode providing an electric potential reference and a sensing electrode providing a measurement point for measuring an electrical potential relative to the reference electrode. The method comprises shielding an electrode by placing a shield near but electric insulated from the electrode, generating an input signal by means of the electrode sensing an electric potential, amplifying the input signal received from the electrode in an integrated amplifier providing a buffered path outputting a buffered output signal, connecting the shield to the output of the integrated amplifier to actively drive the electrical potential of the shield, thereby providing an active shielding of the electrode, frequency shifting the input signal from a basic frequency range to a higher frequency range by means of a first mixer placed in front of the integrated amplifier, and frequency shifting the amplified signal from the higher frequency range back to the basic frequency range by means of a second mixer placed on the output of the integrated amplifier.

BRIEF DESCRIPTION OF THE DRAWINGS

The invention will be described in further detail with reference to preferred aspects and the accompanying drawing, in which.

DETAILED DESCRIPTION OF THE INVENTION

Figure 1:
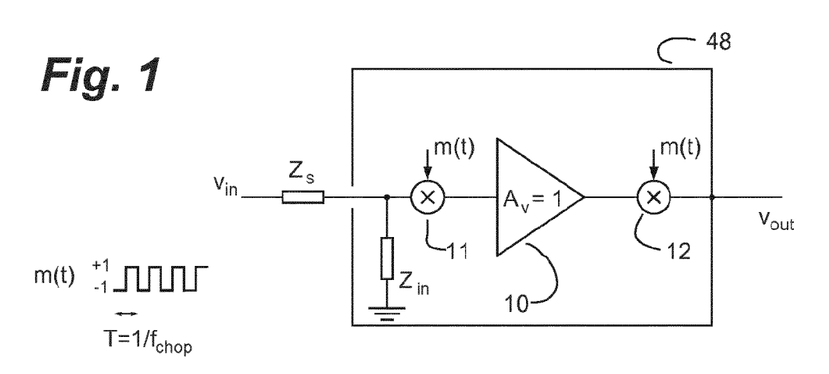
FIG. 1 schematically illustrates an active electrode design according to an embodiment of the invention.

FIG. 1 schematically illustrates an active electrode design according to an embodiment of the invention. A bio-potential signal $V_{in}(t)$ is sensed by a capacitive electrode (not shown) and fed to an input of an integrated amplifier 10. Impedance, $Z_s$, denotes the skin-electrode impedance. On the input of the integrated amplifier 10, the bio-potential signal $V_{in}(t)$ is modulated with a modulation signal (chopper clock), m(t) in a first mixer 11 in front of the integrated amplifier 10. The integrated amplifier 10 has a gain $A_v$ equal to one, whereby the integrated amplifier 10 acts as a buffer, and by applying the same chopper modulation signal, m(t), in a second mixer 12 on the output of the integrated amplifier 10, too, the integrated amplifier 10 and the two mixers 11 and 12 provide a buffered path outputting an output signal $V_{out}(t)$.

The modulation signal m(t) employed in the embodiment shown in FIG. 1 is illustrated as a pulse-width modulated signal having a duty-cycle of 50%, and assumes a unity amplitude of +1 and −1. The chopper frequency, fchop, is selected to ensure that flicker noise in the low frequency range will be substantially eliminated. Impedance, Zin, denotes the finite input impedance. The choppered buffer output Vout(t) is used for driving the active shield placed near said electrode and being electric insulated from said electrode.

Figure 2:
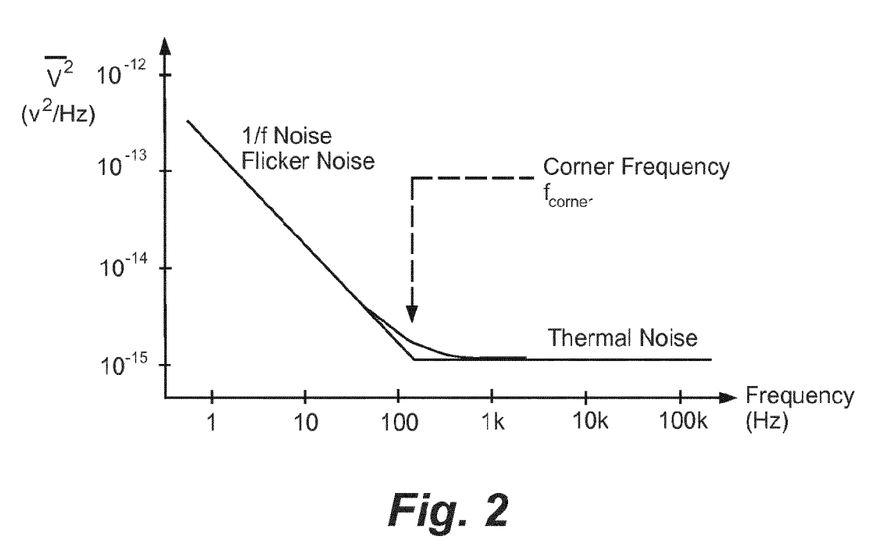
FIG. 2 illustrates for a semiconductor based amplifier the noise spectrum composed by white and pink noise.

With reference to FIG. 2, the noise spectrum composed by white and pink noise for a semiconductor based amplifier is illustrated. The corner frequency fc characterizes the border between the region dominated by the low-frequency flicker noise (pink noise) and thermal noise which is dominating as the higher frequency "flat-band" noise (white noise). Flicker noise occurs in most electronic devices, and provides a limitation on the signal level a circuit may handle. This is illustrated in FIG. 2 where log 10(f) is depicted on the x-axis, and the voltage squared is depicted on the y-axis.

In the current embodiment, the integrated amplifier is realized in a MOSFET transistor layout, and a corner frequency in the level of approximately 200 Hz has been observed. The corner frequency, $f_{corner}$, is the transition between the regions dominated by the low-frequency flicker noise and the higher frequency "flat-band" noise, respectively. Therefor the chopper frequency, $f_{chop}$, has to be chosen so well above the corner frequency, so the frequency shift introduced prior to the integrated amplifier is sufficient to escape the flicker noise region of the integrated amplifier. The modulation frequency providing the frequency shift is greater than the corner frequency, and according to the illustrated embodiment the chopper frequency $f_{chop}$ has been chosen to be in the range from 200 Hz to 2 kHz. Preferably, chopper frequency $f_{chop}$ is in the range from 400 Hz to 1 kHz. When the chopper frequency $f_{chop}$ is higher, the power consumption will be adversely affected.

Figure 6:
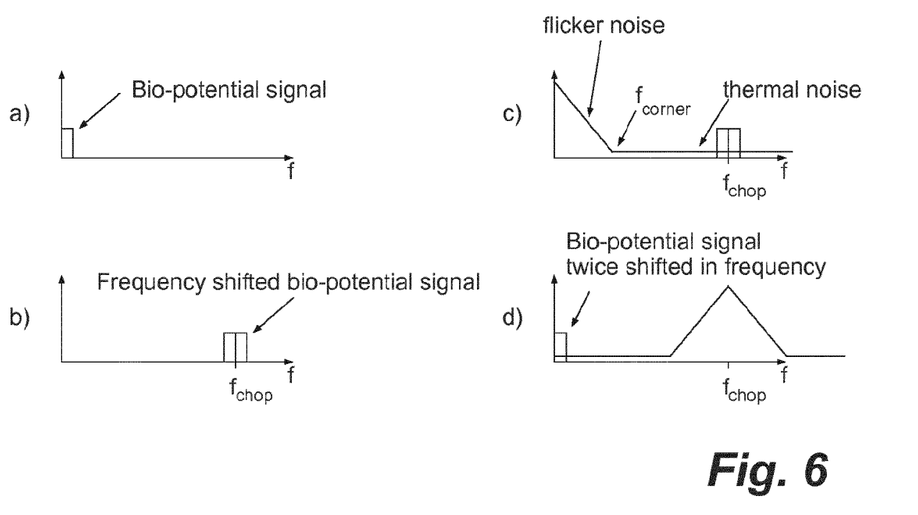
FIGS. 6a-6d illustrate the relative positions of the bio-signal and the noise in the frequency domain for the active electrode design shown in FIG. 1.

For an ear-EEG application the sense electrode will pick up a bio-potential signal Vin(t) having amplitude at approximately 1 µV. The bio-potential signal Vin(t) will in a first use situation have a spectral distribution in a basic frequency range between 0 and 35 Hz—which is schematically illustrated in FIG. 6a. Once modulated with the chopper signal m(t) in the mixer 11, the bio-potential signal Vin(t) will be shifted in frequency so it appears around the chopper frequency at e.g. 1 kHz as is illustrated in FIG. 6b. The integrated amplifier will introduce flicker noise in the spectrum up to the corner frequency e.g. at 200 Hz, while the frequency range above the corner frequency—including the frequency shifted bio-potential signal—will only be affected by white, thermal noise. This is illustrated in FIG. 6c.

In the mixer 12, the output from the integrated amplifier 10 is modulated with the chopper signal m(t), where the bio-potential signal is brought back to the basic frequency range again, while the flicker noise of the amplifier is positioned around the chopper frequency. This is illustrated in FIG. 6d. An appropriate low-pass filtering at a later signal processing stage will remove the flicker originated noise now present in the frequency range around the chopper frequency.

An active electrode design according to the invention may be designed with low input-referred noise, high input impedance and low bias current, low input referred offset, low output impedance, high CMRR and PSRR, and low-power consumption. The actual implementation of an active electrode may be optimized for different applications, for example implantable neural probe array and fabric-based use (dry-contact electrode).

Figure 3:
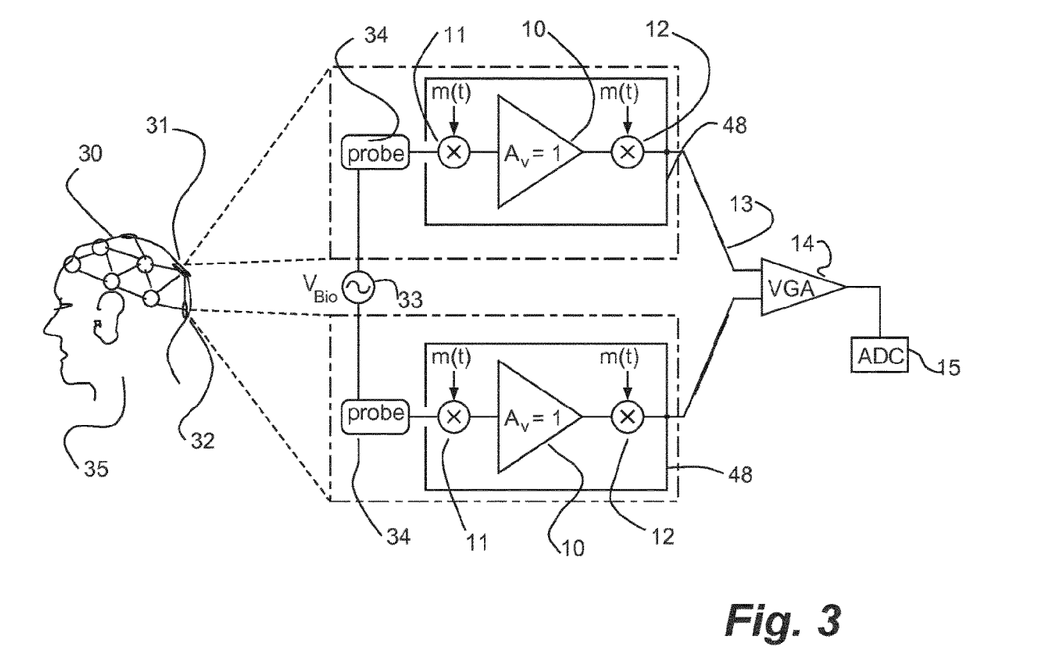
FIG. 3 illustrates schematically a bio-potential monitoring system employing an active electrode design according to an embodiment of the invention.

FIG. 3 shows schematically a bio-potential monitoring system employing an active electrode design according to an embodiment of the invention. A plurality of electrodes is arranged in mesh 30 positioned on the scalp 35 of a user. In another embodiment, the electrodes may be provided on an earplug and data may be collected from the ear canal and processed in a battery driven data processor placed behind the ear. Electrodes 31 and 32 do each include a probe 34 being a capacitive sense electrode and an active shield electrode placed near but spaced apart from the capacitive sense electrode. The input signal picked up by the probes 34 is led to respective amplifiers 10, preferably arranged as a unity gain amplifier. The closed-loop unit-gain amplifiers 10 are connected between the sense electrode and the active shield electrode. With this arrangement, the parasitic capacitor of the sense electrode is effectively reduced, thereby increasing sensitivity.

The output from the closed-loop unit-gain amplifier 10 with chopper modulation is via a shielded cable 13, e.g. a coax cable, fed to a Variable-Gain Amplifier 14 varying the gain based on a control voltage, and further to an Analog-to-Digital Converter 15 converting the amplified VBio signal into a digital representation for further processing. The Variable-Gain Amplifier 14 is a differential amplifier. Shielding is preferred but not crucial/necessary between the front-end integrated circuit containing the closed-loop unit-gain amplifier 10, and the back-end integrated circuit containing the Variable-Gain Amplifier 14 and the Analog-to-Digital Converter 15.

Figure 4:
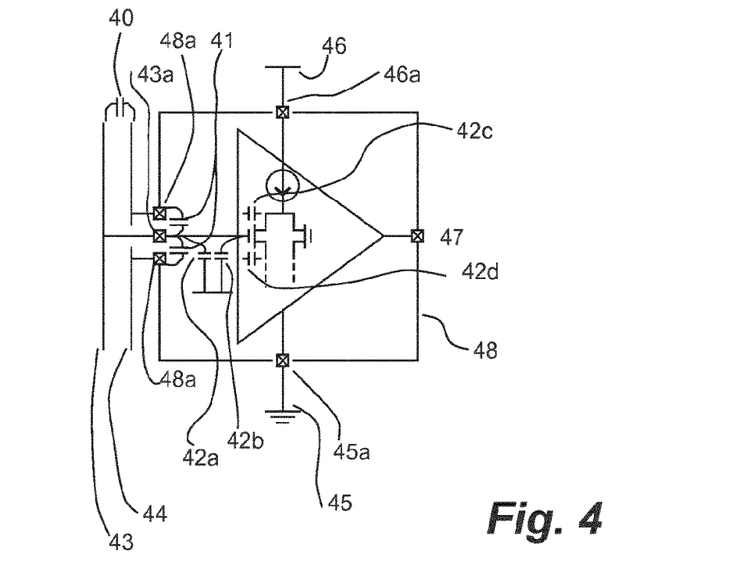
FIG. 4 illustrates schematically one embodiment of a choppered buffer based upon an unit-gain amplifier for use in an electric field sensor according to the invention.

In the following there is provided a technical description of the active electrode using a choppered buffer according to the invention. FIG. 4 illustrates that there exist several major parasitic-capacitance contributors in an active electrode concept. A shield 44 is placed near (and substantially in parallel with) said electrode 43, and the shield 44 is electric insulated from said electrode 43. There is an electric insulator (not shown) between the electrode 43 and the shield 44. This arrangement will cause a capacitive coupling between the electrode 43 and the shield 44. The electrode 43 is connected to the integrated circuit via input pads 43a, and a capacitive parasitic coupling there between may be observed. The shield 44 is via input pads 48a connected to a shield 48 enclosing the integrated circuit, and also here there will be a capacitive parasitic coupling. With shielding by a buffer, electrode parasitic capacitances 40 at the sensing electrode and parasitic capacitances 41 caused by capacitive couplings between the input pads 48a and 43a can be compensated.

The active electrode concept shown in FIG. 4 illustrates that the amplifier is implemented as MOSFET transistors on a substrate (the integrated circuit). The amplifier is connected to a power supply 46 and ground 45 via respective contact pads 46a and 45a, and has an output terminal 47. The output terminal 47 of the integrated amplifier is connected to the shield 48, while the contact pads 45a and 46a are electrical isolated therefrom. The shield 48 is connected to the output terminal 47 of the integrated amplifier to actively drive the electrical potential of the shield 48, thereby providing an active shielding of the electrode 43. Some capacitances are difficult to compensate, because shielding to their bottom node cannot be applied. This count for the parasitic capacitance 42a between the input pad 49a and the substrate, the parasitic capacitance between the transistor gate and the substrate—the gate-to-substrate capacitance 42b, the parasitic capacitance referred between gate and source of the transistor—the gate-to-source capacitance 42c, and the parasitic capacitance between gate and drain of the transistor—the gate-to-drain capacitance 42d. In these circumstances, the objective is to design the circuitry such that the value of the capacitors will be as small as possible.

Figure 5:
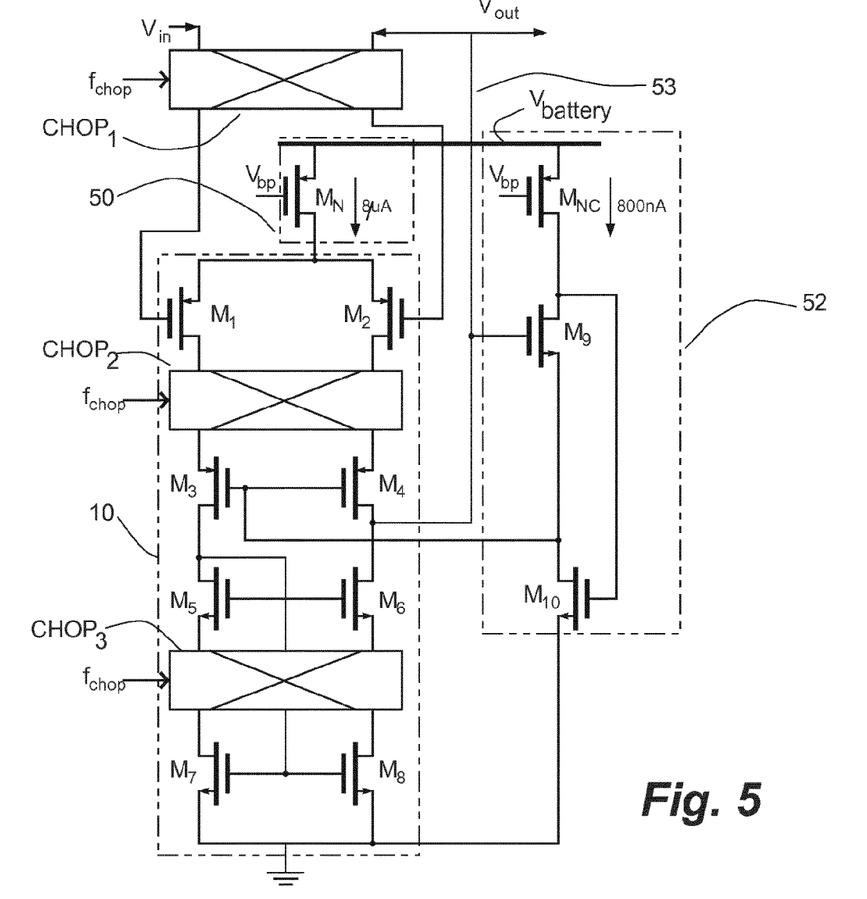
FIG. 5 illustrates a choppered buffer according to one embodiment of the invention.

As shown in FIG. 5, a choppered buffer according to the invention is implemented based on a closed-loop unit-gain amplifier 10 according to the illustrated embodiment. An input transistor pair, M1 and M2, of the closed-loop unit-gain amplifier 10 is minimized in size in order to reduce the input parasitic capacitances and thereby get high impedance. Flicker noise of input transistors M1 and M2 is a non-dominant noise source due to the employed chopper modulation.

A constant current is maintained through the input transistor pair, M1 and M2, through the use of the current source 50 formed by a transistor MN and a voltage source Vbattery. The voltage source Vbattery may according to one embodiment be a coin-cell battery of the type used for hearing aids having nominal supply voltage being approximately 1.2 V.

A bias, Vbp, is applied to the gate of the MOSFET transistor MN controlling the current from the voltage source Vbattery fed to the source of the input transistor pair, M1 and M2.

By maintaining a constant current through the input transistor pair, $M_1$ and $M_2$, and applying the negative feedback of the unity gain configuration, the gate-to-source capacitance 42c (FIG. 4) and gate-to-substrate capacitance 42b (FIG. 4) to the sensor input are minimized.

The illustrated embodiment for implementing the closed-loop unit-gain amplifier 10 with chopper modulation according to the invention employs three chopper switches CHOP1, CHOP2, and CHOP3. The sizes of chopper switches CHOP1, CHOP2, and CHOP3 are optimized for speed and noise, and in this topology, the chopper switches CHOP2 and CHOP3 are arranged inside of the closed-loop unit-gain amplifier 10. Hereby, by using the inherent differential nodes, no extra differential nodes will be required. Furthermore, this will not limit the bandwidth of the closed-loop unit-gain amplifier 10 with chopper modulation.

The input chopper switch CHOP1 receives the sensed bio-potential signal Vin as a first input signal, and the output signal Vout from the closed-loop unit-gain amplifier 10 via a feedback branch 53 as a second input signal. The chopper switch $CHOP_1$ operates at 1 kHz chopper frequency. The chopper signal alternates between +1 and −1 at 50% duty cycle. The bio-potential signal $V_{in}$ has a low bandwidth (normally between 0-40 Hz), but the chopper frequency shall be above the corner, $f_{corner}$ (FIG. 2). Choosing the chopper frequency to be too high, will adversely affect the power consumption of the overall electrode assembly.

The gates of the input transistor pair, M1 and M2, receive respective outputs from the input chopper switch, CHOP1, The constant current from the current source is passed through the input transistor pair, M1 and M2 via respective source terminals, and the drains of the input transistor pair, M1 and M2, are connected to respective terminals on the second chopper switch, CHOP2.

The two outputs from the chopper switch, CHOP2, are connected to respective source terminals of a MOSFET transistor pair, M3 and M4. The transistor pair, M3 and M4, forms a source follower (common-drain amplifier) being a Field Effect Transistor amplifier topology, typically used as a voltage buffer.

MOSFET transistors $M_5$, $M_6$, $M_7$ and $M_8$ form a cascoded current mirror circuit, which would be recognized by a person skilled in the art as being a standard component in an operational amplifier. The cascoded current mirror circuit is a two-stage amplifier composed of a transconductance amplifier followed by a current buffer. The third chopper switch $CHOP_3$ is arranged in between the two stages of the cascoded current mirror circuit. The cascoded current mirror circuit improves input-output isolation as there is no direct coupling from the output to input.

Three MOSFET Transistors $M_{NC}$, $M_9$ and $M_{10}$ are arranged as an extra source follower. The three MOSFET Transistors $M_{NC}$, $M_9$ and $M_{10}$ are connected to the voltage source $V_{battery}$ and operated as a level shifter providing lower dc bias to the transistors $M_3$ and $M_4$ forming the source follower.

Figure 7:
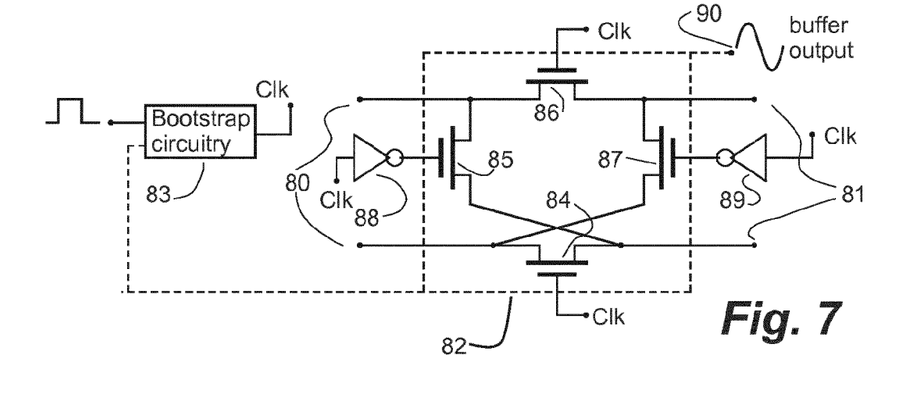
FIG. 7 illustrates one embodiment of a chopper switch used in the choppered buffer shown in FIG. 5.

FIG. 7 illustrates one embodiment of the chopper switch $CHOP_1$, $CHOP_2$, $CHOP_3$ used in the choppered buffer topography shown in FIG. 5. The chopper switch has a pair of input terminals 80 and a pair of output terminals 81. The chopper switch is shielded by bulks by means of a shield 82, and includes four transistor switches 84, 85, 86, and 87—all controlled by a clock signal, Clk. For the transistor switches 85 and 87, the clock signal, Clk is received via respective inverters 88 and 89, whereby the transistor switches 84 and 86 closes when the clock signal is high, and the transistor switches 85 and 87 closes when the clock signal is low. The inverters 88 and 89 are NOT gates implementing logical negation. Thereby, the four transistor switches 84, 85, 86, and 87 ensures that a first terminal of the pair of input terminals 80 alternately connected to a first and a second terminal of the output of the pair of output terminals 81. The second terminal of the pair of input terminals 80 alternately connected to the second and the first terminal of the output of the pair of output terminals 81.

By connecting the bulks or the shield 82 to the buffer output 90, all the transistor switches 84, 85, 86, and 87 are shielded to eliminate the body effects and extra current flow through the bulk nodes. Therefore the bias current will not significantly change when input common-mode voltage varies. In addition, the chopping clock is bootstrapped to keep the overdrive voltage and thereby the "ON" resistance of the transistor switches 84, 85, 86, and 87 substantially constant. In such a way, the current noise and the thermal noise are insensitive to input common-mode voltage. A bootstrap circuitry 83 clock signal and the output buffer signal via the shield 82 and delivers on the output the chopper clock signal, Clk, used to open and close the transistor switches 84, 85, 86, and 87. The bootstrap circuitry 83 deliberately intends to alter the input impedance.

Figure 10:
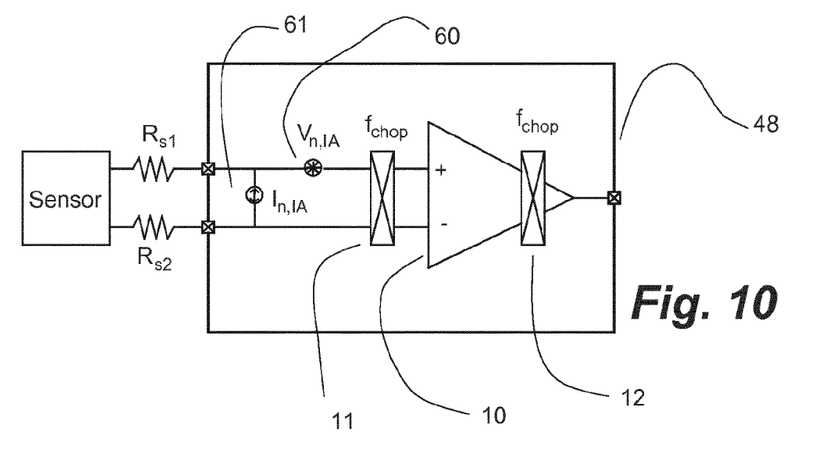
FIG. 10 shows the excess noise sources at the input of chopper amplifier.

As illustrated in FIG. 10, the noise issues may be separated into two categories: voltage-domain noise and current-domain noise. FIG. 10 show the excess noise sources at the input of chopper amplifier as shown in FIG. 5. A man skilled in the art will understand that the problems caused by current noise are highly depending on the value of source impedance. Since the skin-electrode impedance is relatively large, and subject to large variations, in the dry-contact acquisition analog front-end, both two noises deserve our concerns.

Voltage-Domain Noise

FIG. 10 shows the excess noise sources at the input of chopper amplifier. $R_{sx}$ denotes the skin-electrode resistance. The main voltage noise contributors 60 include the input transistor pair, $M_1$ and $M_2$, and the final transistor pair M7 and M8 in the cascoded current mirror circuit, due to the high voltage gain from the these MOSFETs gates. The voltage noise may be expressed as a result of the flicker noise and the thermal noise, and the offset and flicker noise is theoretically removed from low frequency signal band, due to the chopper modulation. The dominant component of the residue noise is thermal noise, $V_{noise}$, of MOSFETs and may be expressed as follows:

$$V\text{noise} \approx \sqrt{(1+gm7/gm1)(8kT/gm1)BW} \qquad (1)$$

where BW denotes the bandwidth of interest, $g_{mi}$ the transconductance of MOSFETs $M_i$, k is Boltzmann's constant, and T is the absolute temperature of the component. Within the bandwidth between 0.5-100 Hz, the integrated noise is approximately 0.29 $\mu V_{rms}$ when the chopper frequency is selected to be 1 kHz and the transconductance of the dominating MOSFETs has been optimized in order to minimizing the thermal noise.

From equation (1) it is seen that the noise voltage $V_{noise}$ is proportional with the reciprocal value of the square root of the transistor transconductance. It has been found that current consumption of 8 µA and noise of 29 nV/$\sqrt{Hz}$ as acceptable in terms of power and noise budget of the system, which has been indicated in FIG. 5 by operating the closed-loop unit-gain amplifier 10 through the use of the current source 50 providing 8 µA.

Current-Domain Noise

Bias current 61 gives rise to offset across the source impedance. For bio-signal sensor amplifiers, the major sources of bias current include leakage in ESD protection circuitry, gate leakage of input MOSFETs and base current of bipolar junction transistors, chopping activities as well as PCB leakage. The dominant contributors include leakage of ESD protection circuitry and current flow caused by periodic chopping activities.

The leakage of ESD protection circuitry is highly dependent on the ESD techniques and circuitry properties. Therefore it exists in all the amplifiers and it's hard to be completely avoided. Periodic chopping activities give rise to dynamic current flow through the chopper switches and switch-capacitor resistance. By definition, the bias current is the average current over a relatively long time at the input node. For the CMOS chopper amplifiers, such kind of current could be the dominant bias current source over the others.

It has been observed that the excess noise normally can be regarded as negligible in amplifiers with low-source-impedance, for instance, 10 kΩ~20 kΩ of wet electrodes. However for high-source-impedance, for instance, several hundred kilo ohm to several mega ohm of dry-contact electrode, the imperfections like dc offset and corresponding output noise will be regarded as problematic.

By applying appropriate design optimization strategies, all the switches may advantageously be shielded to eliminate the body effects and extra current flow through the bulk nodes. Therefore the bias current will not significantly change when input common-mode voltage varies. In addition, the chopping clock is bootstrapped to keep the overdrive voltage and thereby the 'on' resistance of the switches approximately a constant. In such a way, the current noise and the thermal noise are insensitive to variation in the input common-mode voltage.

By ensuring a well optimization of the choppered buffer according to one embodiment of the invention, the bias current is quite low. The chopper switches are naturally shielded by the buffer and there exist no significant potential differences between sources and drains as well as bulks in the switches. Therefore there is no current path in the chopper. The current noise for the choppered buffer according to one embodiment of the invention has been observed in the level about 0.3 fA/$\sqrt{Hz}$. With a 1MΩ resistor connected, the excess noise density contribution would be 0.3 nV/$\sqrt{Hz}$.

The Common-Mode Rejection Ratio (CMRR) of a differential amplifier is the rejection by the device of unwanted input signals common to both input leads, relative to the wanted difference signal. A high CMRR is required when a differential signal must be amplified in the presence of a disturbing common-mode input. Power Supply Rejection Ratio (PSRR) is defined as the ratio of the change in supply voltage in the op-amp to the equivalent (differential) output voltage it produces. The output voltage will depend on the feedback circuit. Chopper modulation has been found to not only reduce the noise but also to contribute to the improvement of the CMRR and the PSRR.

The Common-Mode Rejection (CMR) of the amplifier without chopper modulation has been observed to be −73.3 dB and with chopper modulation the CMR is improved to −107.9 dB, almost 35 dB enhancement in CMRR. Furthermore, the Power Supply Rejection (PSR) has been improved with chopper modulation from −48 dB to −97.3 dB, an almost 49 dB enhancement in PSRR. This has been observed with a capacitance load of 10 pF at the output node for a frequency band (wanted input signal) below 100 Hz.

According to the invention there is provided a new choppered buffer employed in the active electrode design. Compared with conventional and state-of-art designs, an active electrode with choppered buffer exhibits several attractive advantages. Thanks to the unit-gain configuration, a well shielding property can be permitted. As a consequence, ultra-high input impedance is obtainable, and thereby high CMRR of input impedance network could be realized. Chopper modulation shielded by the buffered output leverages the voltage-domain and the current-domain accuracies, reaching a good trade-off compared to conventional techniques using buffer and chopper amplifier. Besides, a significant benefit resulting from chopper modulation is the improved CMRR and PSRR between two buffer channels, which could be quite useful to enhance the noise immunity against surrounding interferences. The subsequent differential amplifier could filter out the accompanying chopper spikes and ripples at expense of extra amount of power. The active electrode with choppered buffer is very suitable for use in high-quality bio-recording systems.

Figure 8:
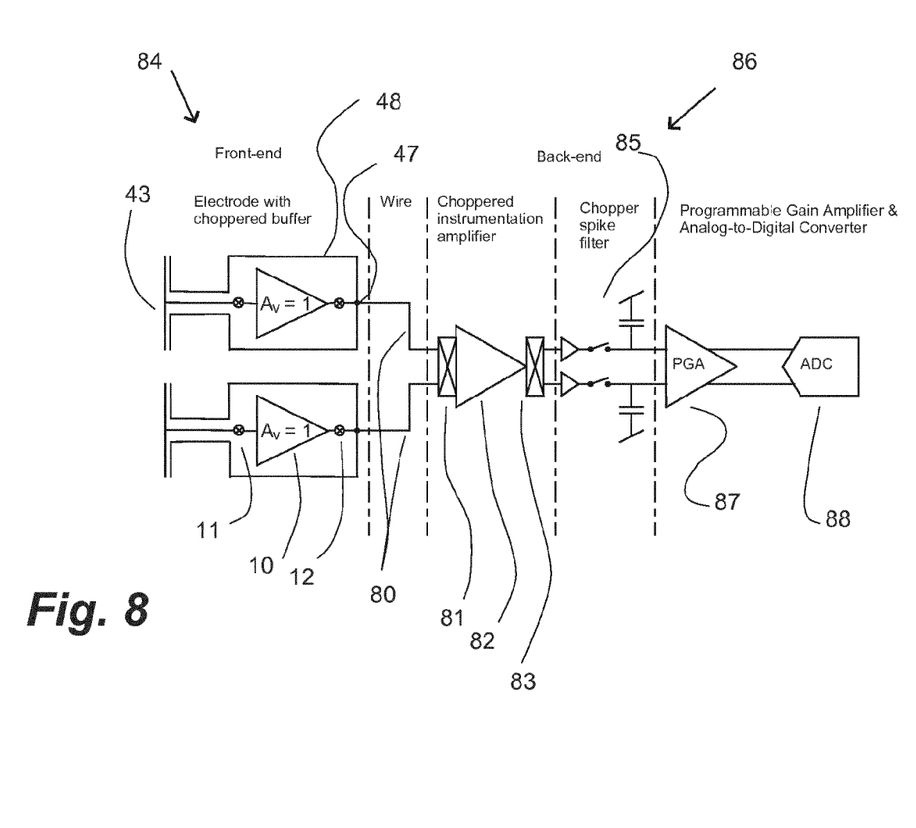
FIG. 8 illustrates one embodiment of a sensor system based upon two active sensors according to the invention.

FIG. 8 shows an embodiment of a sensor system based upon two active electrodes according to the invention. The shown sensor system includes a front-end module 84 being connected to a back-end module 86 via a set of wires 80. The front-end module 84 includes in the illustrated embodiment a pair active electrodes 43 with choppered buffer as described with reference to FIG. 1. The choppered buffer is based upon the integrated amplifier 10 has a gain, Av, equal to one, and two mixers 11 and 12 applying the same chopper modulation signal, m(t). Furthermore the output terminal 47 of the choppered buffer is connected to the shield 48 enclosing the integrated circuit. Preferably, the active electrodes operate in differential mode—which means that one of the electrodes acts as reference.

The back-end module 86 has a choppered instrumentation amplifier based upon an integrated amplifier 82 having a gain for amplifying the bio-potential signal from the active electrodes, and two mixers 81 and 83 applying the same chopper modulation signal, n(t). The chopper modulation signal, n(t) is applied in order to avoid amplifying the flicker noise in the integrated amplifier 82.

The chopper clock signal n(t) is preferably a square-wave signal that contains odd harmonics at fch, 3 fch, 5 fch, and as most of the energy of the chopper ripple is located at the first harmonics, fch, the higher harmonics may be eliminated by applying a Chopper Spike Filter (CSF) 85 providing a low pass or band pass filtering effect. The Chopper Spike Filter 85 includes a sample and hold circuit provided by a switch and a capacitor, where the switch is driven by sampling pulses. The Chopper Spike Filter 85 removes glitch caused by the chopper switches. Two branches fed from the output of choppered instrumentation amplifier 81-83, but with reverse polarity, has been included in order to generate a fully differential output is fed a Programmable Gain Amplifier (PGA) 87 and an Analog-to-Digital Converter (ADC) 88, from where the signal is supplied to a not-shown microcontroller for processing.

The choppered instrumentation amplifier 82 may in one embodiment be provided in front-end module 84 and thereby included within the active shielding. Then the number of thin wires 80 connecting the front-end module 84 to a back-end module 86 may be reduced from four to two (shielded) wires. These wires carries supply voltage, ground, clock and signal and may in a specific embodiment have a length of 10 mm.

Figure 9:
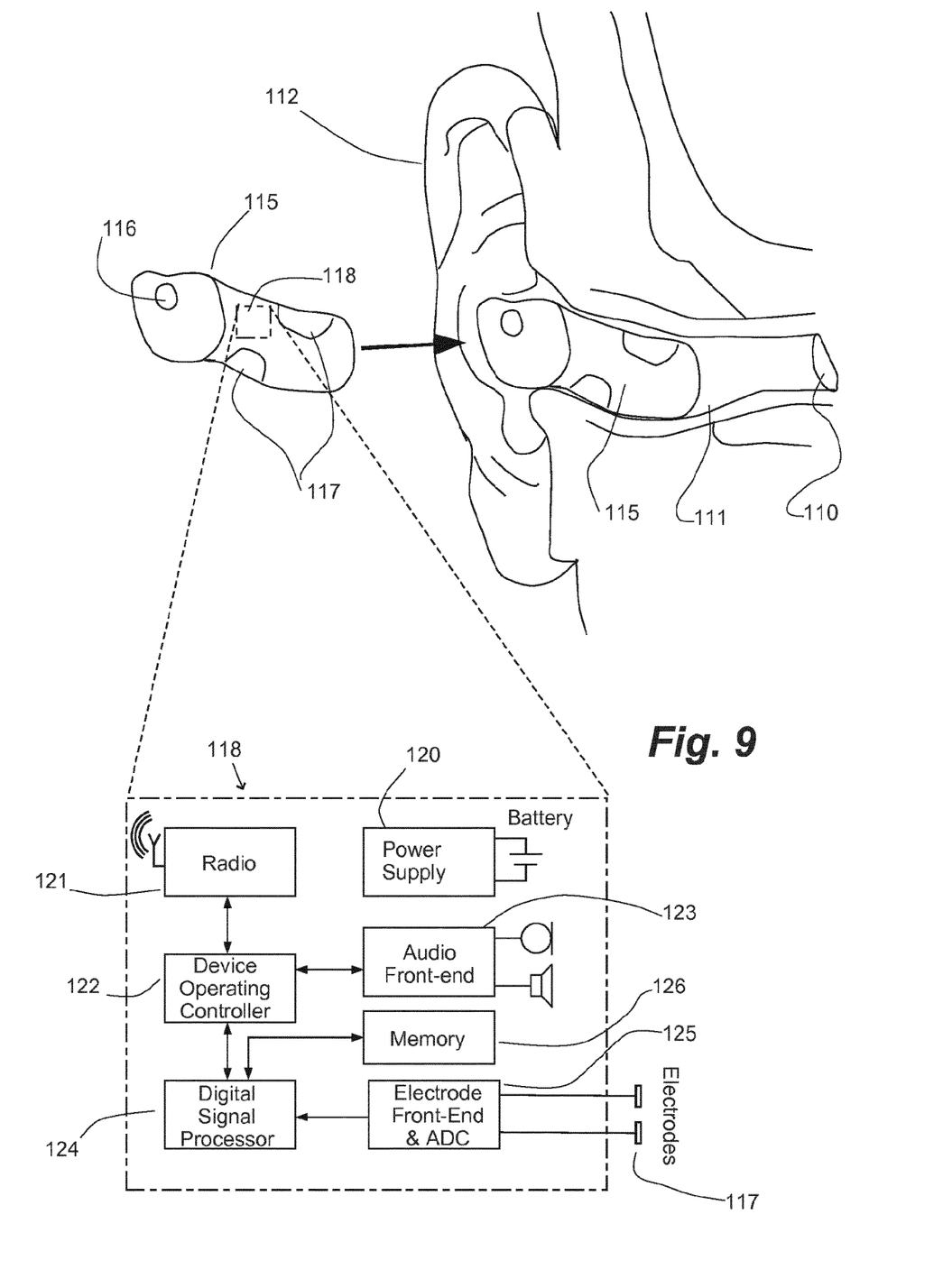
FIG. 9 illustrates one embodiment of an EEG device according to one aspect of the invention.

FIG. 9 shows an ear EEG device 115 according to one aspect of the invention. The ear EEG device 115 that can be worn inside the ear of a person to be monitored, e.g. for detecting Hypoglycemia, e.g. like a per se known In-The-Canal (ITC) hearing aid. Furthermore, the device will allow healthcare personal to remote monitor or record EEGs for several days at a time. Healthcare personal would then be allowed to monitor patients who have regularly recurring problems like seizures or micro-sleep. The ear EEG device 115 will not interfere with normal life, because the ear EEG device 115 has an acoustic vent 116 so the wearer will be able to hear. After a while, the wearer forgets that he wears the ear EEG device 115. The ear EEG device 115 is on its outer surface provided with two active electrodes 117 according to the invention. Internally the ear EEG device 115 contains an electronic module 118.

The ear EEG device 115 is formed to fit into the external auditory canal 111 of the wearer, and defines a cavity in the external auditory canal 111 together with the tympanic membrane 110, and the cavity is opened by means of the acoustic vent 116 extending through the entire length of the ear EEG device 115. Preferably the ear EEG device 115 does not extend beyond the pinna 112.

The electronic module 118 is shown schematically in enlarged view in the dotted box 118. The electronic module 118 includes a power supply 120 based upon a standard hearing aid battery for powering the electronics. The two electrodes 117 provided on the surface of the ear EEG device 115 pick up a potential and delivers the data via a module 125 operating as electrode frontend and Analog to Digital Converter (ADC) to a digital signal processor 124. Details of the electrode frontend and ADC module 125 has been explained with reference to FIG. 8. The digital signal processor 124 receives the amplified and digitized signal for processing. According to one embodiment, the digital signal processor 124 analyses the EEG signal picked up for detecting hypoglycemia by monitoring the brain wave frequency, and if the brain wave frequency falls beyond a predefined interval, this may indicate that a medical emergency may arise. Hypoglycemia is a medical emergency that involves an abnormally diminished content of glucose in the blood. Upon detection of abnormal brain wave activities, the digital signal processor 124 communicates these findings to a device operating controller 122.

The device operating controller 122 is responsible for several operations and has an audio front-end module 123 including a microphone and a speaker. With the microphone, the device operating controller 122 is able to pick up audio samples and classify the current sound environment. Furthermore, the device operating controller 122 may have access to real time clock information—either from an internal clock module or from a personal communication device (e.g. a smartphone) accessible via a radio module 121. The personal communication device and the radio module 121 may establish a wireless communication link by means of a short range communication standard, such as the Bluetooth™ Low Energy standard. The device operating controller 122 adjusts the predefined interval for normal the brain wave activity in dependence to the real time clock information and the sound environment classification. With the speaker, the device operating controller 122 is able to alert the wearer of the ear EEG device 115 that medical emergency may arise and that precautionary actions have to be taken.

The number of electrodes has so far been identified as a pair of active electrodes operating in differential mode. However two or more active electrodes may be acting as sensing electrodes for measuring the electric potential difference relative to an active electrode acting as a common reference electrode. The electrodes will operate in a unipolar lead mode.

The ear EEG device 115 may in a further embodiment operate as a hearing aid if the processor is provided with a gain for alleviating a hearing loss of the wearer. The ear EEG device 115 may advantageously be integrated into an In-The-Canal (ITC) hearing aid, a Receiver-In-Canal (RIC) hearing aid or another type of hearing aid.

The invention claimed is:

1. An active electrode component having an electrode for sensing a bio potential and adapted for providing a bio potential signal, and furthermore comprising:
   a shield placed adjacent to and electrically insulated from said electrode;
   an integrated amplifier component adapted for providing a buffered signal path and comprising:
   a first mixer formed on an integrated circuit chip for frequency shifting the bio potential signal from a basic frequency range to a higher frequency range,
   an integrated amplifier formed on said integrated circuit chip and receiving the frequency shifted signal from the first mixer, and having a unit-gain, and
   a second mixer formed on said integrated circuit chip for frequency shifting an output signal from the integrated amplifier from the higher frequency range to the basic frequency range,
   the integrated amplifier component being configured as a chopper modulation amplifier outputting a buffered output signal;
   wherein an output of the integrated amplifier component is connected to the shield,
   whereby the shield adjacent to the electrode receives the buffered output signal,
   the integrated amplifier component being adapted for actively driving an electrical potential of the shield and thereby providing an active shielding of the electrode,
   wherein said integrated amplifier has the unit gain maintained at least in part by a feedback signal on a feedback branch from a first point downstream of said second mixer to a second point upstream of said first mixer.

2. The active electrode according to claim 1, wherein said frequency shift is adapted to avoid a flicker noise region of the integrated amplifier.

3. The active electrode according to claim 1, wherein a corner frequency defines a transition between low-frequency flicker noise and higher frequency white noise, and wherein a modulation frequency providing the frequency shift is greater than the corner frequency.

4. The active electrode according to claim 3, wherein the modulation frequency is lower than ten times the corner frequency.

5. A method for sensing an electric potential difference in a sensor system having at least one set of electrodes including a reference electrode providing an electric potential reference and an active electrode component according to claim 1, the method comprising:

generating an input signal by means of said active electrode component sensing the bio potential;

amplifying the input signal received from said electrode in said integrated amplifier;

connecting said shield to said output of the integrated amplifier to actively drive the electrical potential of said shield, thereby providing an active shielding of said sensing electrode;

frequency shifting the input signal from the basic frequency range to the higher frequency range by means of said first mixer placed in front of the integrated amplifier;

and frequency shifting the amplified signal from said higher frequency range back to said basic frequency range by means of said second mixer placed on the output of the integrated amplifier.

6. The method according to claim 5, said method further comprising:

receiving in a differential amplifier inputs from said sensing electrode and said reference electrode, and generating in said differential amplifier an output signal representing the electrical potential difference between said sensing electrode and said reference electrode.

7. The method according to claim 5, wherein said integrated amplifier generates an output signal replicating the input signal fed to integrated amplifier.

8. The method according to claim 5, wherein said frequency shifting by means of said first mixer is adapted to avoid a flicker noise region of the integrated amplifier.

9. The active electrode according to claim 3, wherein the modulation frequency is no greater than 10 times said corner frequency.

10. The active electrode according to claim 9, wherein the modulation frequency is at least twice said corner frequency and no more than five times said corner frequency.

11. The active electrode according to claim 1, wherein a chopping frequency of said first mixer is less than 1,000 Hz.

12. A sensor system for sensing an electric potential difference, comprising: at least one set of electrodes including a reference electrode providing an electric potential reference;

a sensing electrode providing a measurement point for measuring an electrical potential relative to said reference electrode; and a differential amplifier receiving input from said sensing electrode and said reference electrode and generating an output signal representing the electrical potential difference between said sensing electrode and said reference electrode;

wherein at least one electrode of said least one set of electrodes being an active electrode component having an electrode for sensing a bio potential and adapted for providing a bio potential signal, and furthermore comprising:

a shield placed adjacent to and electrically insulated from said sensing electrode;

an integrated amplifier component adapted for providing a buffered signal path and comprising:

a first mixer for frequency shifting the bio potential signal from a basic frequency range to a higher frequency range, an integrated amplifier receiving the frequency shifted signal from the first mixer, and having a unit-gain maintained at least in part by a feedback signal on a feedback branch from a first point downstream of said integrated amplifier to a second point upstream of said integrated amplifier, and a second mixer for frequency shifting an output signal from the integrated amplifier from the higher frequency range to the basic frequency range, the integrated amplifier component being configured as a chopper modulation amplifier outputting a buffered output signal;

wherein an output of the integrated amplifier component is connected to the shield, the integrated amplifier component being adapted for actively driving the electrical potential of the shield and thereby providing an active shielding of the sensing electrode, whereby the shield adjacent to the sensing electrode receives the buffered output signal, and wherein said first point is downstream of said second mixer and said second point is upstream of said first mixer.

13. The sensor system according to claim 12, wherein said least one set of electrodes is a pair of electrodes both being active electrodes.

14. The sensor system according to claim 12, wherein said at least one set of electrodes is provided as a plurality of pairs of active electrodes.

15. The sensor system according to claim 12 in which a plurality of sensing electrodes are measuring the electric potential difference relative to a common reference electrode.

16. The sensor system according to claim 15, wherein said plurality of sensing electrodes being active electrodes.

17. The sensor system according to claim 12, wherein sensing electrodes are measuring the electric potential difference relative to a linear combination of the other electrodes.

18. The sensor system according to claim 12, wherein said at least one set of electrodes being adapted to sense Electrocardiography (ECG) signals or Electroencephalography (EEG) signals.

19. The sensor system according to claim 12, wherein a corner frequency defines a transition between low-frequency flicker noise and higher frequency white noise, and wherein said first and second mixers both operate at a chopping frequency that is greater than said corner frequency but less than 10 times said corner frequency.

20. The sensor system according to claim 19, wherein said chopping frequency is at least 2 times said corner frequency but not greater than 5 times said corner frequency.

21. The sensor system according to claim 12, wherein a chopping frequency of said first mixer is less than 1,000 Hz.

22. An active electrode component having an electrode for sensing a bio potential and adapted for providing a bio potential signal, and furthermore comprising:

a shield placed adjacent to and electrically insulated from said electrode;

an integrated amplifier component adapted for providing a buffered signal and comprising:

a first mixer formed on an integrated circuit chip for frequency shifting the bio potential signal from a basic frequency range to a higher frequency range, an integrated amplifier formed on said integrated circuit chip and receiving the frequency shifted signal from the first mixer, and having a unit-gain, and a second mixer formed on said integrated circuit chip for frequency shifting an output signal from the integrated amplifier from the higher frequency range to the basic frequency range, the integrated amplifier component being configured as a chopper modulation amplifier outputting a buffered output signal;

wherein an output of the integrated amplifier component is connected to the shield, the integrated amplifier component being adapted for actively driving an electrical potential of the shield and thereby providing an active shielding of the electrode, whereby the shield adjacent to the electrode receives the buffered output signal, wherein said first mixer receives two input signals and provides first and second chopped output signals, and said integrated amplifier is a differential amplifier having first and second inputs each coupled to receive a respective one of said chopped output signals, and wherein said second input of said first mixer is connected to receive a feedback signal derived from the output of said integrated amplifier.

23. A sensor system for sensing an electric potential difference, comprising:

at least one set of electrodes including a reference electrode providing an electric potential reference;

a sensing electrode providing a measurement point for measuring an electrical potential relative to said reference electrode; and a differential amplifier receiving input from said sensing electrode and said reference electrode and generating an output signal representing the electrical potential difference between said sensing electrode and said reference electrode;

wherein at least one electrode of said least one set of electrodes being an active electrode component having an electrode for sensing a bio potential and adapted for providing a bio potential signal, and furthermore comprising:

a shield placed adjacent to and electrically insulated from said electrode;

an integrated amplifier component adapted for providing a buffered signal and comprising:

a first mixer for frequency shifting the bio potential signal from a basic frequency range to a higher frequency range, an integrated amplifier receiving the frequency shifted signal from the first mixer, and having a unit-gain, and a second mixer for frequency shifting an output signal from the integrated amplifier from the higher frequency range to the basic frequency range, the integrated amplifier component being configured as a chopper modulation amplifier outputting a buffered output signal;

wherein an output of the integrated amplifier component is connected to the shield, the integrated amplifier component being adapted for actively driving the electrical potential of the shield and thereby providing an active shielding of the sensing electrode, whereby the shield adjacent to the sensing electrode receives the buffered output signal, wherein said first mixer receives two input signals and provides first and second chopped output signals, and said integrated amplifier is a differential amplifier having first and second inputs each coupled to receive a respective one of said chopped output signals, and wherein said second input of said first mixer is connected to receive a feedback signal derived from the output of said integrated amplifier.

\* \* \* \* \*